(12) United States Patent
Simek et al.

(10) Patent No.: US 8,653,811 B2
(45) Date of Patent: Feb. 18, 2014

(54) PIPELINE INSPECTION TOOL WITH OBLIQUE MAGNETIZER

(75) Inventors: James Simek, Sandy, UT (US); Tod Baker, Clearfield, UT (US); Mark Gregoire, Sandy, UT (US)

(73) Assignee: TDW Delaware Inc., Wilmington, DE (US)

( * ) Notice: Subject to any disclaimer, the term of this patent is extended or adjusted under 35 U.S.C. 154(b) by 458 days.

(21) Appl. No.: 12/572,752

(22) Filed: Oct. 2, 2009

(65) Prior Publication Data

US 2010/0327859 A1 Dec. 30, 2010

Related U.S. Application Data

(60) Provisional application No. 61/220,734, filed on Jun. 26, 2009.

(51) Int. Cl.
*G01N 27/72* (2006.01)

(52) U.S. Cl.
USPC .............................. 324/220; 324/219; 324/228

(58) Field of Classification Search
USPC .......................................................... 324/220
See application file for complete search history.

(56) References Cited

U.S. PATENT DOCUMENTS

| | | |
|---|---|---|
| 3,483,466 A | 12/1969 | Crouch et al. |
| 3,786,684 A | 1/1974 | Wiers et al. |
| 4,258,318 A | 3/1981 | Furukawa et al. |
| 5,454,276 A | 10/1995 | Wernicke |
| 5,565,633 A | 10/1996 | Wernicke |
| 6,009,756 A | 1/2000 | Willems et al. |
| 6,100,684 A | 8/2000 | Ramaut |
| 6,107,795 A | 8/2000 | Smart |
| 6,820,653 B1 | 11/2004 | Schempf et al. |
| 7,362,097 B2 | 4/2008 | Brown et al. |
| 7,548,059 B2 | 6/2009 | Thompson et al. |
| 2001/0022514 A1 | 9/2001 | Light et al. |
| 2004/0095137 A1 | 5/2004 | Kwun et al. |

(Continued)

FOREIGN PATENT DOCUMENTS

| | | |
|---|---|---|
| JP | 59058358 A | 4/1984 |
| JP | 60080760 | 5/1985 |

(Continued)

OTHER PUBLICATIONS

Morimoto, Kazuo, JP 60080760, PTO Translation, p. 1-10.*

(Continued)

*Primary Examiner* — Thomas F Valone
(74) *Attorney, Agent, or Firm* — Gable Gotwals

(57) ABSTRACT

A pipeline inspection tool has an even number "n" of spiraled pole magnets spaced equidistant apart and spanning the length of the tool. Each pole magnet, which preferably has a conformable upper surface, is rotated or spiraled about the tool body so that a second end of each pole magnet is offset a predetermined amount "α" relative to a first end of that same pole magnet. The amount of rotation α applied to each of the pole magnets produces a magnetic field oblique to the central longitudinal axis of the tool body (and therefore the pipe) and one that covers 360° of the internal wall surface of the pipe. A helical-shaped array of magnetic flux sensors may be arranged about the tool body and substantially equidistant between adjacent pairs of pole magnets. The tool detects axially oriented, circumferentially oriented, and volumetric anomalies and allows for single pass inspection.

17 Claims, 6 Drawing Sheets

(56) References Cited

U.S. PATENT DOCUMENTS

| | | | |
|---|---|---|---|
| 2009/0078048 A1 | 3/2009 | Alers et al. | |
| 2010/0117635 A1 | 5/2010 | Hoyt | |
| 2010/0199767 A1 | 8/2010 | Ganin | |
| 2010/0327858 A1* | 12/2010 | Simek et al. | 324/220 |

FOREIGN PATENT DOCUMENTS

| | | |
|---|---|---|
| JP | 60080760 A | 5/1985 |
| JP | 62067447 A | 3/1987 |
| WO | WO 2006/048290 | 5/2006 |
| WO | WO 2006/069684 | 7/2006 |

OTHER PUBLICATIONS

PTO 12-1043 English translation of Morimoto JP 59-058358 Japanese patent, Dec. 2011, p. 1-10.*

PTO Translation, Morimoto, Kazuo, JP 60080760, translated Dec. 2011. p. 1-10.*

Van Den Berg et al., "Development of an Electromagnetic Acoustic Transducer for Inspecting the Wall Thickness of Offshore Risers From the Inside, 1988."

Netherlands Patent Office, "Search Report issued by the Netherlands Patent Office dated Dec. 16, 2010 in Patent Application No. 2004962."

Austrian Patent Office, "First Office Action issued by the Austrian Patent Office dated Feb. 25, 2011 in Patent Application No. 10222010."

Search Report issued by the United Kingdom Intellectual Property Office dated Aug. 10, 2010 in application GB1010491.7 (2 pgs).

Search Report issued by the United Kingdom Intellectual Property Office dated Aug. 25, 2010 in application GB1010493.3 (1 pg).

Search Report issued by the Netherlands Patent Office dated Oct. 6, 2010 in Patent Application No. NL 2004963.

* cited by examiner

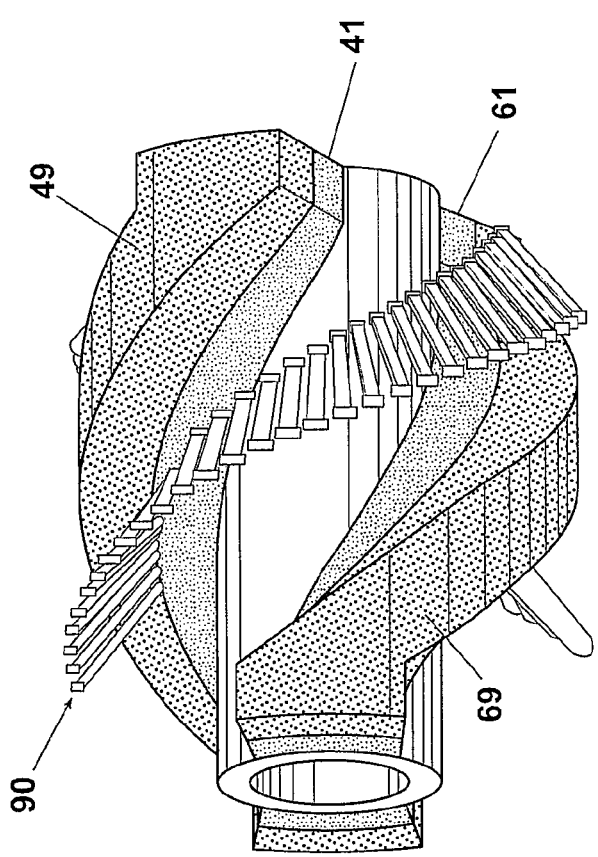
*Fig. 9*
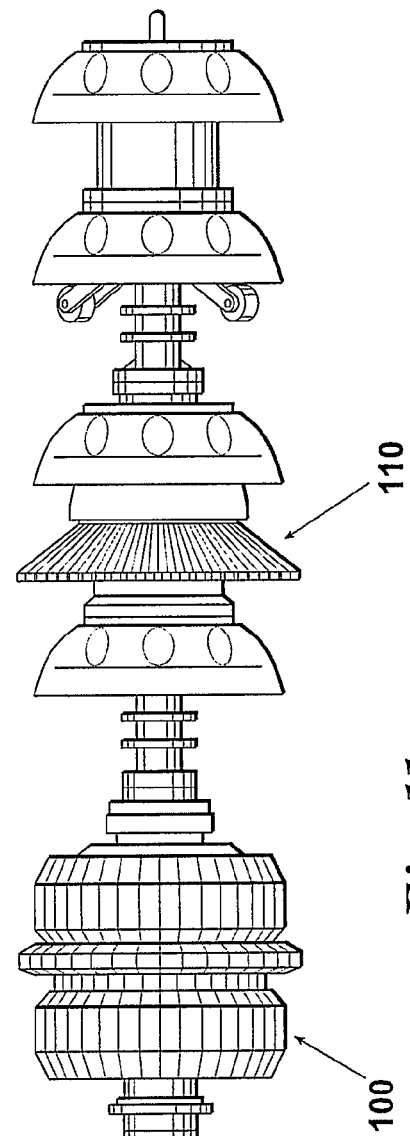
*Fig. 11*
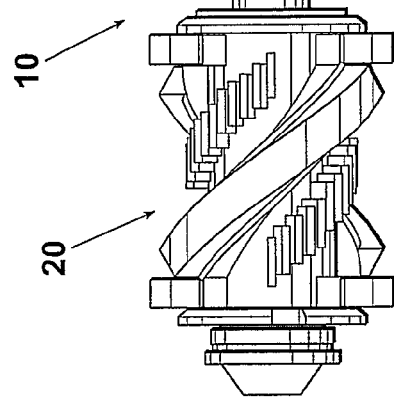

PIPELINE INSPECTION TOOL WITH OBLIQUE MAGNETIZER

REFERENCE TO PENDING APPLICATIONS

This application claims the benefit of U.S. Provisional Patent Application No. 61/220,734, filed Jun. 26, 2009.

FIELD OF INVENTION

This invention relates generally to inspection tools designed to detect anomalies in tubing, piping and pipelines and, more particularly, to inline inspection tools employing magnetic flux leakage detection techniques.

BACKGROUND OF THE INVENTION

Many installed pipelines may be inspected using the Magnetic Flux Leakage (MFL) technique, primarily for the purpose of identifying metal loss anomalies. Magnetic flux leakage has been shown to respond in predictable ways to anomalies in the wall of the pipeline as the principal axis of the metal loss anomaly and field angle are varied. Both experimental and modeling results have been used to confirm this effect, which is also widely described in the literature.

Due in part to limitations imposed by data acquisition, data storage and magnetic circuit designs, most in-line inspection tools have employed axially oriented magnetizers (see e.g., U.S. Pat. No. 6,820,653 to Schempf et al.). However, the present axial field magnetizer designs make identification and quantification of extremely narrow axial features difficult, or in some cases, impossible. For these feature classes, a solution using a magnetic field in the circumferential or transverse direction, have been marketed and placed in service over the past decade by pipeline inspection providers. However, due to the constraints of physics, the performance and accuracy of these transverse magnetic flux inspection (TFI) tools in general is less than that of axial field tools for general metal loss anomalies.

Additionally, these TFI tools typically require a minimum of two magnetizer assemblies in order to achieve adequate coverage, making it impractical or difficult to incorporate these into an existing axial MFL tool.

For those pipelines that may have extremely narrow metal loss features, or certain classes of seam weld anomalies, standard axial field tools do not provide adequate detection and quantification capabilities. In these cases, for MFL based tools, either the initial or supplemental surveys are performed using a TFI tool. While TFI tools may be capable of detecting extremely narrow anomalies and certain seam weld anomalies, they also detect all of the remaining volumetric metal loss features typically found in pipelines, complicating the process of identifying the targeted anomaly classes.

One of the earliest TFI arrangements is described in U.S. Pat. No. 3,483,466 to Crouch et al. Crouch discloses a pair of electromagnets arranged perpendicular to each other with detectors such as magnetometers or search coils positioned on each side of the magnets. Other than the use of permanent magnets and hall device-type sensors, Crouch's arrangement remains as the basis for most modern implementations. Additionally, some designs involve segmented or individual discrete magnets that, in most cases, retain the transverse or circumferential field direction. For example, U.S. Pat. No. 3,786,684 to Wiers et al. discloses individual magnets arranged in arrays oblique to the pipe axis with the fields of each array perpendicular the others. However, this arrangement limits the field to sections and areas between the poles of each individual magnet. Furthermore, the short pole spacing required for a Wiers-type implementation decreases the length of the magnetic circuit, thereby causing the tool to suffer from velocity effects, and also masks, distorts or degrades data quality at welds, dents, or other anomalies.

Other designs involve elaborate complex geometries, multiple magnetizer sections, and elaborate mechanical arrangements such as helical drives, gears and wheels designed to induce spiral or helical motion of the magnetizer section. For example, U.S. Pat. No. 5,565,633 to Wernicke discloses a mechanically complicated device for use with magnetizer sections having two or more magnetic circuits and a plethora of sensing units. In one embodiment, the magnet blocks are arranged with spirally situated parallel poles. In another embodiment, the magnet blocks are twisted pole pairs displaced axially. Both embodiments require mechanically induced rotation in order to achieve full coverage of the inner pipe surface. Similar to Wernicke, U.S. Pat. No. 6,100,684 to Ramuat discloses a substantially transverse field magnetization arrangement that involves multiple magnetizer sections and a complex arrangement of wheels to induce helical motion of the sections and achieve overlapping or full coverage of the pipe wall. U.S. Pat. No. 7,548,059 to Thompson et al. includes two skids (poles) that incorporate fixed magnets arranged in closely spaced pairs to create a nominally transverse field spiraling around the pipe. This tool—which includes a variety of moving parts such as supporting tendons, pulleys, and springs—requires much added complexity in order to be flexible enough to accommodate bends in the pipeline. Furthermore, the magnets in this arrangement induce a field between two parallel poles, forming a single closed loop circuit between the poles of the individual discrete magnet blocks.

Similar to Thompson et al., the magnets used in the prior art are described as being blocks, with no reference to a supple or conformable upper surface used for the magnet block. Use of a rigid contact arrangement for the magnetic circuit degrades data quality by introducing air gaps or variable reluctance zones in the magnetic field path at dents or along welds and other upsets that may be present within the pipeline. For certain classes of features, disturbances created in the ambient field mask or otherwise distort the flux leakage signals present because of the features of interest. Any magnetic anomalies existing within dents and weld zones are of greater significance due to their presence within these zones and, as such, represent areas in which data quality is critical.

Additionally, the prior art requires the use of a large number of poles or surfaces in an intimate contact arrangement to the pipe wall surface. This arrangement can result in extremely high frictional forces or resistance to motion being experienced by the magnetizer assembly, thereby inhibiting or preventing its use in applications requiring lower friction.

There is a need for a MFL tool that provides full coverage of the inner pipe wall surface without the need for mechanically complicated structures; produces a field that detects axially-oriented, circumferentially-oriented and volumetric features; generates similar responses from features regardless of whether the features are axially or circumferentially oriented; eliminates or reduces velocity effects as well as signal masking, disruptions and distortion at welds, dents and other upsets; navigates pipeline obstructions, bends and reductions; and allows pipeline surveys to be accomplished in a single pass.

SUMMARY OF THE INVENTION

A pipeline inspection tool made according to this invention includes a magnetizer assembly having a cylindrical tool body, at least two radial discs, and an even number "n" of pole magnets arranged about an external surface of the cylindrical tool body. Each pole magnet—which preferably has a conformable upper surface, such as a brush-like surface, between the magnet and the internal wall surface of the pipe—extends the length of the cylindrical body located between the two radial discs. The spacing between adjacent pole magnets is about 360°/n, "n" being the number of pole magnets employed. The magnetic flux paths radiate from the magnet poles, diverging in opposite directions and returning to an opposing pole in similar fashion.

The pole magnets are rotated or spiraled about the cylindrical tool body so that a second end of each pole magnet is offset a predetermined amount "α" relative to a first end of that same pole magnet. The amount of rotation α applied to each of the pole magnets produces a magnetic field oblique to the central longitudinal axis of the tool body (and therefore the pipe). The amount of rotation α, which may range from 30° to 150°, is preferably an amount of rotation that is effective for producing a magnetic field that covers 360° of the internal wall surface of a pipe lying opposite the tool body.

A helical-shaped array of magnetic flux sensors may be arranged about the cylindrical tool body and substantially equidistant between adjacent pairs of pole magnets. Preferably, a degree of overlap in the sensor array is provided, with a first end of the array of magnetic flux sensors extending a distance "Δ" past a line containing a second end of the array.

It is an object of this invention to provide a magnetic flux leakage (MFL) tool that responds to a broad range of anomalies capable of generating magnetic flux leakage signals. Another object of this invention is to provide a MFL tool capable of 360° coverage of the internal pipe wall using a single magnetizer without the need for multiple magnetizer sections, magnetizers, or relative motion between the sensors or sections to achieve detection of nominally axially oriented features. Another object of this invention is to provide a MFL tool capable of detecting volumetric-type metal loss features in conjunction with ultrasonic, electro-magnetic acoustic transducer, or magnetostrictive detection methods. Yet another object of this invention is to provide a MFL tool that produces a magnetic field which generates a substantially similar response from axially-oriented or transversely-oriented features as well as generating detectable responses from volumetric-type metal loss features. Still yet another object of this invention is to provide a MFL tool that eliminates or reduces the mechanical motion effects upon flux leakage signals at welds, dents and other upsets. Still another object of this invention is to provide a MFL tool that detects and quantifies the extremely narrow axial classes of anomalies, with the added benefit of doing so in conjunction with an existing axial field magnetizer, providing greater overall accuracy in metal loss anomaly quantification. Another object of this invention is to minimize the number of moving parts and assemblies incorporated into the MFL tool. Still yet another object of this invention is to provide a means for the MFL tool to compress in order to pass by obstructions, bends and reductions in a pipe. A further object of this invention is provide a single tool in which the pipeline survey may be done in a single pass, reducing the amount of effort required by both the pipeline operator and inspection personnel for onsite operations, data handling, data analysis, and final report generation.

BRIEF DESCRIPTION OF THE DRAWINGS

FIG. 9 is a view of an embodiment of the oblique magnetizer assembly that includes a helical-shaped sensor array mounted from one end of the magnetizer to the other, providing complete coverage of the internal pipe wall surface and incorporating a degree of overlap to accommodate any tool rotation that may take place.

FIG. 11 is a view of an inline inspection tool that includes the oblique magnetizer assembly, an axial magnetizer and a deformation sensing section.

DETAILED DESCRIPTION OF THE PREFERRED EMBODIMENTS

Figure 1:
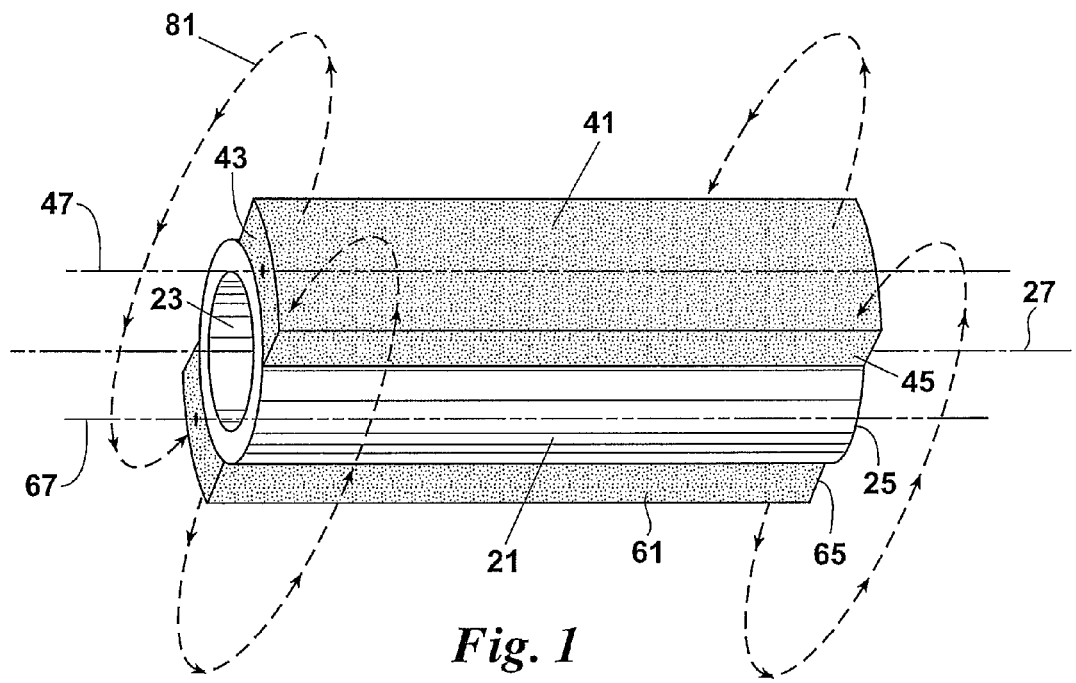
FIG. 1 is an isometric view of a transversed oriented magnetizer design. The direction of the magnetic field is circumferential or transverse to the longitudinal axis of the pipe.
Figure 2:
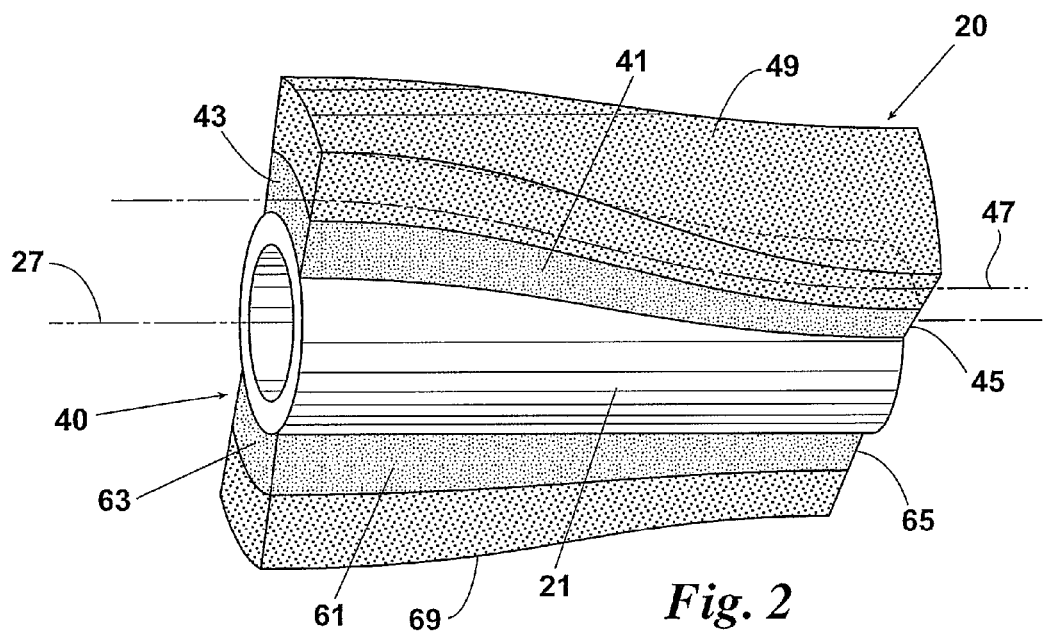
FIG. 2 is an isometric view of an embodiment of an oblique magnetizer assembly according to this invention that utilizes a spiral magnet pole design. The pole magnets are rotated or spiraled about 30° and include a flexible or conformable upper surface.
Figure 3:
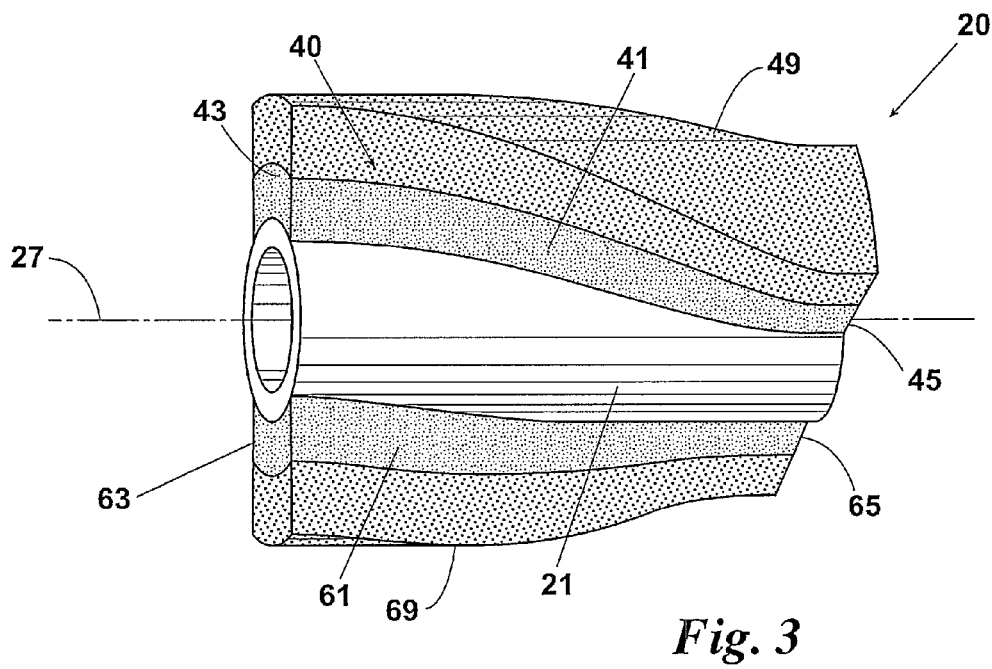
FIG. 3 is a view of another embodiment of the oblique magnetizer assembly in which the pole magnets are rotated about 60°.
Figure 4:
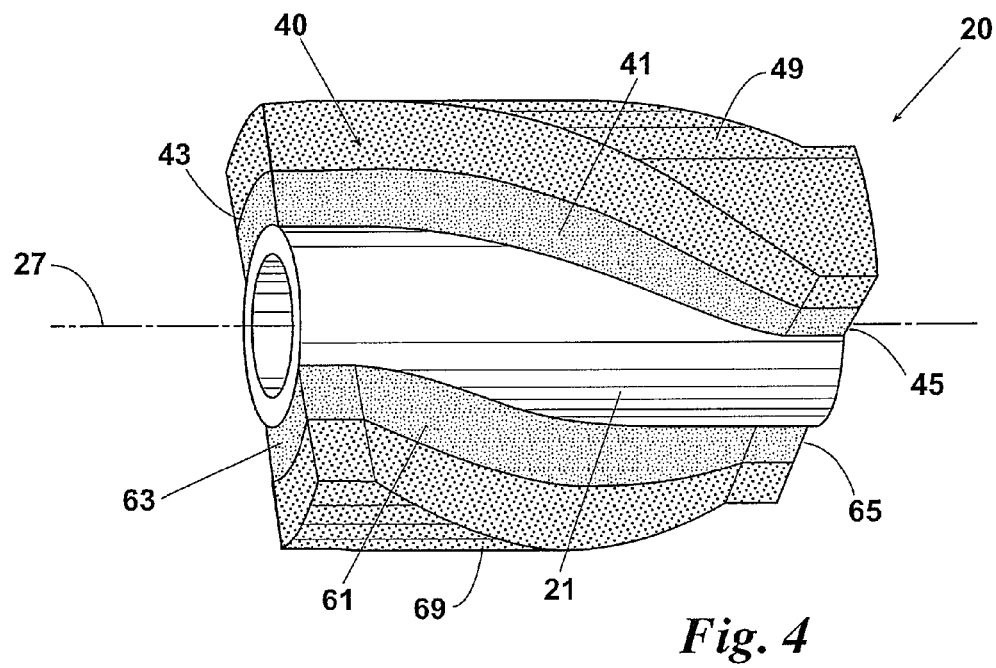
FIG. 4 is a view of yet another embodiment of the oblique magnetizer assembly in which the pole magnets are rotated about 90°.
Figure 5:
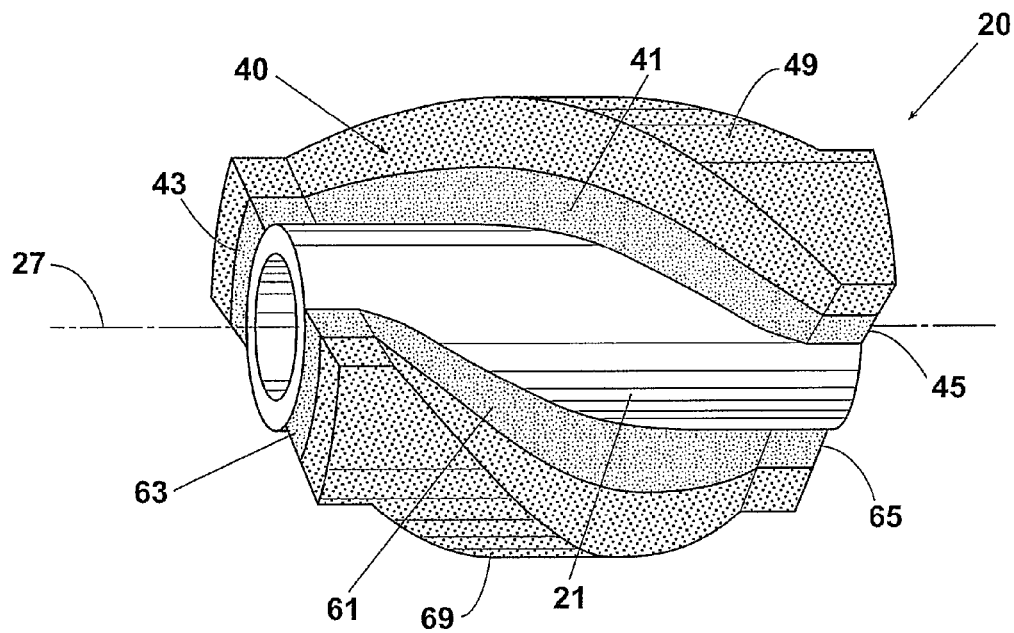
FIG. 5 is a view of still yet another embodiment of the oblique magnetizer assembly in which the pole magnets are rotated about 120°.

Preferred embodiments of a magnetic flux leakage (MFL) tool made according to this invention will now be described by making reference to the drawings and the following elements illustrated in the drawings:

10 In-line inspection tool
20 MFL tool/oblique magnetizer
21 Cylindrical tool body
23 First end of 21
25 Second end of 21
27 Longitudinal axis of 21
31 Radial disc
40 Magnetic circuit
41 Pole magnet
43 First end of 41
45 Second end of 41
47 Longitudinal centerline of 41
49 Conformable upper surface
51 Brushes
61 Pole magnet
63 First end of 61
65 Second end of 61
67 Longitudinal centerline of 61
69 Conformable upper surface
71 Brushes
80 Magnetic field
81 Magnetic flux path of field 80

90 Sensor array
91 First end of 90
93 Second end of 90
100 Axial magnetizer
110 Deformation sensing section Referring first to FIG. 1, a north pole magnet 41 and a south pole magnet 61 are arranged about 180° opposite one another on a cylindrical tool body 21 so that the respective longitudinal centerline 47, 67 of each pole magnet 41, 61 is parallel to the longitudinal centerline 27 of the cylindrical tool body 21 (and therefore parallel to a central longitudinal axis of the pipe being inspected). Although pole magnets 41, 61 differ from prior art implementations in that, for example, each magnet 41, 61 extends along the entire length of the cylindrical body 21, their axial orientation as illustrated here is typical of prior art implementations. Arranged in this way, pole magnets 41, 61 generate a circumferential or transverse magnetic field relative to the pipe wall—as illustrated by magnetic flux paths 81—and multiple magnetizer sections are required to provide complete coverage of the internal wall surface of the pipe.

Referring now to FIGS. 2 to 6, an oblique magnetizer assembly 20 according to this invention includes a magnetic circuit 40 that has two spiraled pole magnets 41, 61 arranged about 180° opposite one another on cylindrical tool body 21. Each pole magnet 41, 61 extends between a first end 23 and second end 25 of the cylindrical tool body 21. Additional pairs of spiraled pole magnets 41, 61 may also be employed, with each spiraled pole magnet 41 or 61 extending between the ends 23, 25 of cylindrical tool body 21 and spaced 360°/n from its adjacent and opposite pole magnet 61, 41 ("n" being an equal to the number of pole magnets 41, 61 employed). The pole magnets 41, 61 preferably have a flexible or conformable upper surface 49, 69, respectively, that helps reduce friction forces and minimize velocity effects as the oblique magnetizer assembly 20 travels through the interior of a pipe. The conformable upper surface 49, 69 also allows the magnetizer assembly 20 to compress a sufficient amount in order to pass by internal obstructions, bends, and reductions in the pipe that might otherwise damage the magnetizer assembly 20 or slow or prevent its passage.

Figure 6:
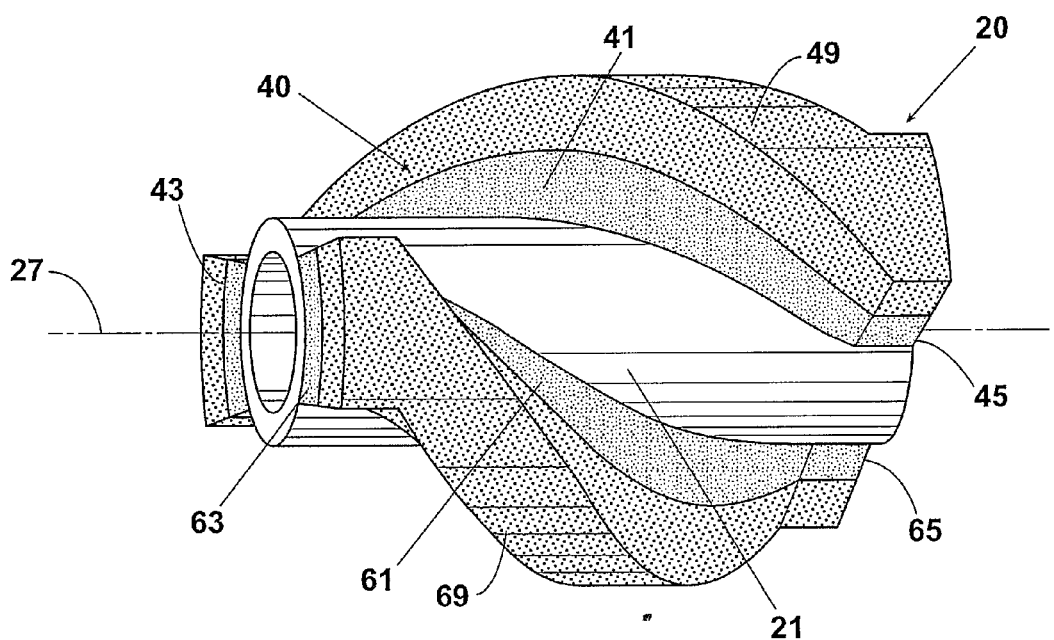
FIG. 6 is a view of yet another embodiment of the oblique magnetizer assembly in which the pole magnets are rotated about 150°.
Figure 7:
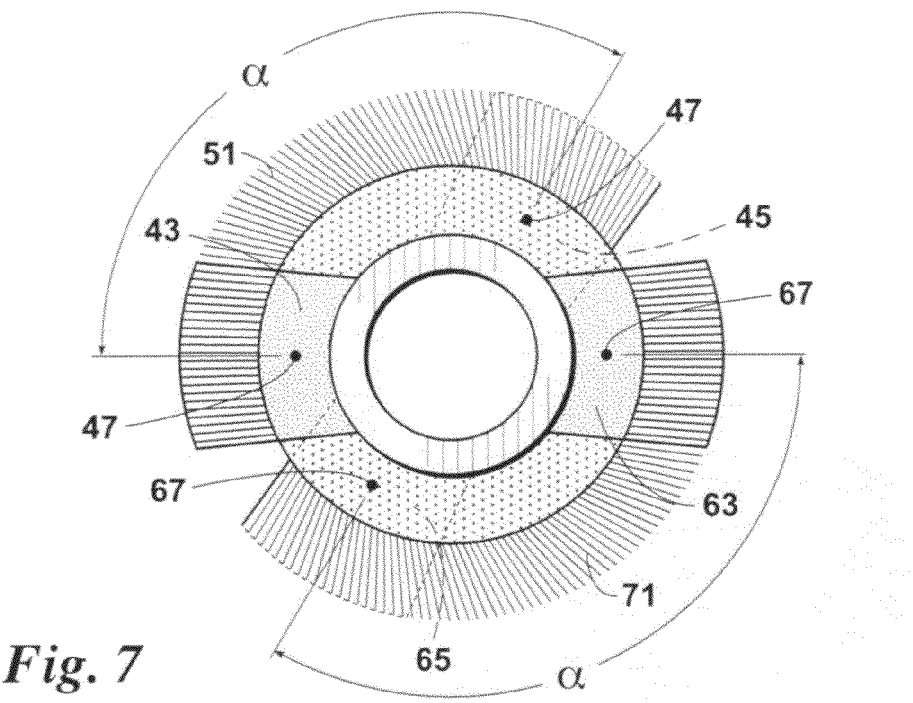
FIG. 7 is an end view of another embodiment of the oblique magnetizer assembly of illustrating the relationship between the two ends of the spiraled or rotated pole magnets. In this example, the pole magnets are rotated about 135°. The conformable upper surface of each pole magnet includes a bristle or brush-type surface.

The rotation amount of the pole magnets 41, 61 depends on the amount of rotation required to achieve full coverage of the internal pipe wall surface. Going through the sequence from FIG. 2 to FIG. 6, the pole magnets 41, 61 are each rotated or spiraled in incremental amounts, for a nominal rotation of about 150 degrees (as illustrated in FIG. 6). When rotated, the second end 45, 65 of the pole magnet 41, 61 is offset by a predetermined angle or amount α relative to its respective first end 43, 63 (see FIG. 7). Because of this rotation amount α, the respective longitudinal centerline 47, 67 of each spiraled pole magnet 41, 61 is non-parallel to the central longitudinal axis 27 of the cylindrical tool body 21. The rotation of pole magnets 41, 61 also helps induce a sufficient amount of rotation of magnetizer assembly 20 as it travels through the interior of the pipe.

Figure 8:
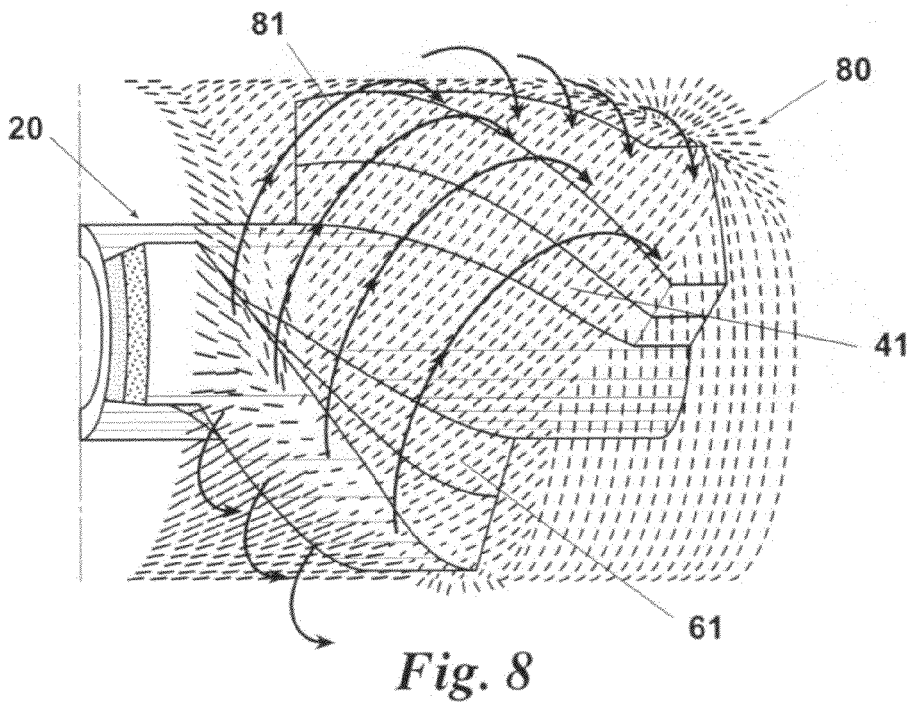
FIG. 8 illustrates field results from the oblique magnetizer arrangement. The field direction is diagonal, or oblique, to the longitudinal axis of the pipe.

FIG. 8 illustrates the magnetic field 80 generated from a prototype of oblique magnetizer assembly 20, which was configured similar to the magnetizer assembly 20 shown in the rotation sequence of FIGS. 2 to 6. Unlike prior art in-line inspection tools, the direction of magnetic field 80 is diagonal or oblique to the pipe axis rather than circumferential or transverse, with magnetic flux paths 81 emanating from the poles 41, 61 and traveling in opposite directions to reach a corresponding pole 61, 41. The magnetic flux lines 81 generated by each pole magnet 41, 61 are guided to the path of least resistance: into the pipe wall and toward the adjacent pole magnet 61, 41. The angle of the magnetic field 80 is generally perpendicular to the flux lines 81 formed by the magnetic poles 41, 61 and generally parallel to a line forming the shortest distance between the magnet poles 41, 61. The direction of magnetic field 80 within the extents of poles 41, 61 may range from 30 to 60 degrees relative to the pipe axis.

Figure 10:
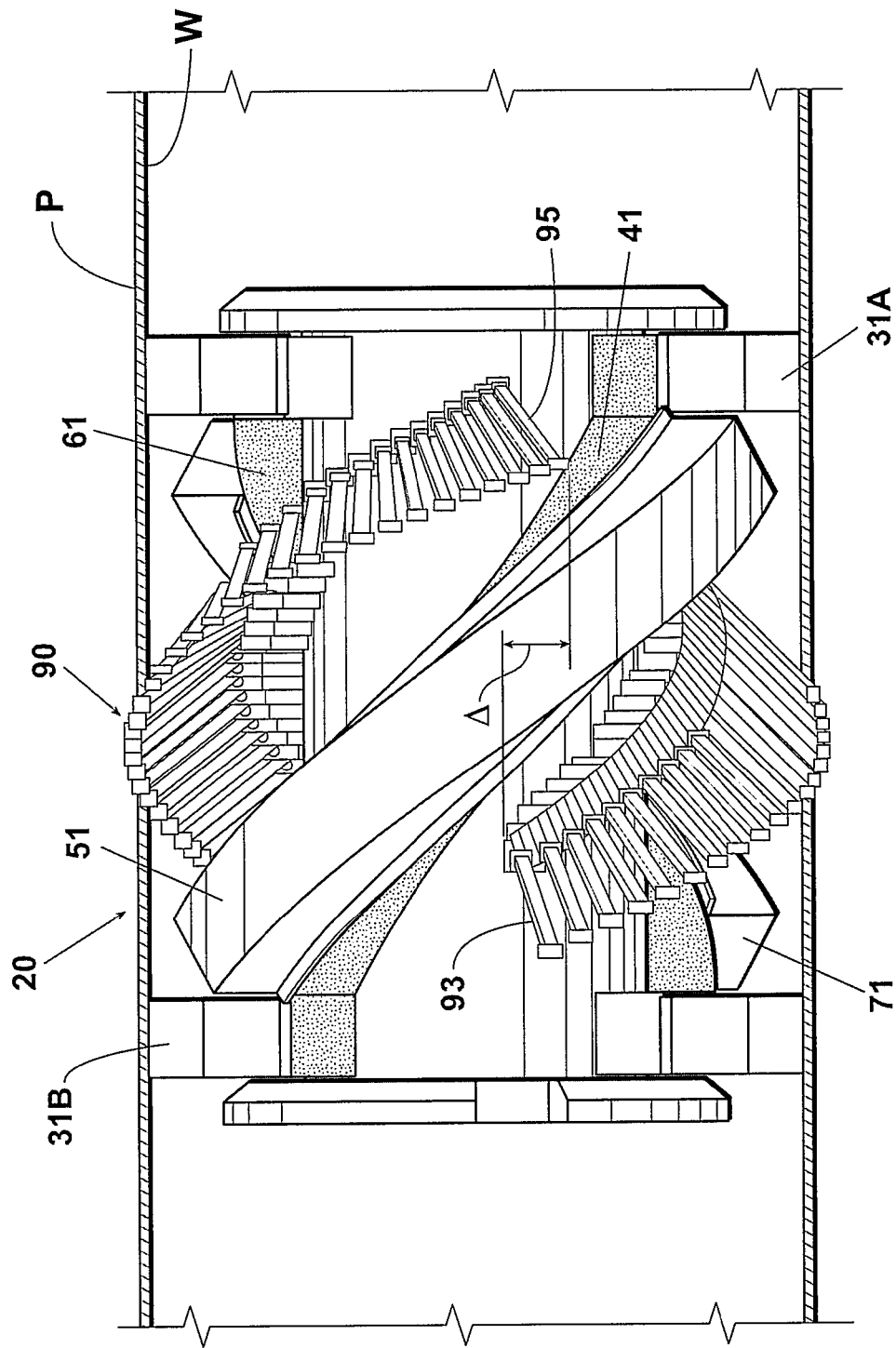
FIG. 10 is a view of the oblique magnetizer assembly of FIG. 8 encased in a pipe section.

Referring now to FIGS. 9 & 10 oblique magnetizer assembly 20 may include a helical-shaped sensor array 90 located substantially equidistant between rotated pole magnets 41, 61 and arranged to provide complete coverage of the internal wall surface W of pipe P and accommodate any rotation of magnetizer assembly 20 that may take place. The individual sensors in sensor array 90 may be of a kind well-known in the art for detecting magnetic flux leakage signals. Sensor array 90 preferably extends between the first end 23 and second end 25 of cylindrical body 21 (and therefore between the respective ends 43, 45 and 63, 65 of pole magnets 41, 61) and incorporates a degree of overlap Δ between a first end 91 and second end 93 of sensor array 90. The conformable upper surfaces 49, 69 of the pole magnets 41, 61 (see e.g. FIG. 6) may be in the form of brushes 51, 71. Radial discs 31A & B help propel and center magnetizer assembly 20 as it moves forward in pipe P under differential pressure.

The final configuration of oblique magnetizer assembly 20 may include any current combination of data sets, including but not limited to deformation, high level axial MFL, internal/external discrimination, inertial data for mapping, and low level or residual MFL. In one preferred embodiment of an inline inspection tool 10 incorporating oblique magnetizer assembly 20, the tool 10 includes an axial magnetizer 100 and a deformation sensing section 110 (see FIG. 11).

While a MFL tool that includes an oblique magnetizer and helical sensor array has been described with a certain degree of particularity, many changes may be made in the details of construction and the arrangement of components without departing from the spirit and scope of this disclosure. An MFL tool according to this disclosure, therefore, is limited only by the scope of the attached claims, including the full range of equivalency to which each element thereof is entitled.

What is claimed is:

1. A pipeline inspection tool comprising:
a magnetizer assembly having a cylindrical tool body and at least two pole magnets having opposite polarity;
each pole magnet being spaced apart from the other pole magnet and spiraled less than half a turn about said cylindrical tool body to create a single oblique magnetic field around said cylindrical tool body;
wherein no induced rotation of the magnetizer assembly is required to provide 360° coverage by the single oblique magnetic field of an internal pipeline wall.

2. A pipeline inspection tool according to claim 1 further comprising the amount of spiraling being in a range of 30° to 150°.

3. A pipeline inspection tool according to claim 1 further comprising at least one pole magnet having a flexible upper surface.

4. A pipeline inspection tool according to claim 3 further comprising said flexible upper surface being brushes.

5. A pipeline inspection tool according to claim 1 further comprising an array of magnetic flux sensors arranged about said cylindrical tool body and between said two pole magnets.

6. A pipeline inspection tool according to claim 5 further comprising said array of magnetic flux sensors being arranged in a helix-shaped arrangement.

7. A pipeline inspection tool according to claim 6 further comprising a first end of said array of magnetic flux sensors extending a distance "Δ" past a line containing a second end of said array.

8. A pipeline inspection tool according to claim 1 further comprising the single oblique magnetic field having a direction in a range of 30° to 60° relative to a central longitudinal axis of said cylindrical tool body.

9. A pipeline inspection tool according to claim 1 wherein each pole magnet spans the distance between a forward and a rearward radial disc of the cylindrical tool body.

10. A pipeline inspection tool comprising:
a magnetizer assembly having a cylindrical tool body and a single pair of pole magnets having opposite polarity;
each pole magnet in said single pair of pole magnets being spaced apart from one another, spiraled about said cylindrical tool body, and having a first end and a second end with the first end lying on a horizontal cylindrical segment of said cylindrical tool body opposite that of the first end of the other pole magnet to provide a magnetic circuit which creates a magnetic flux flowing in helical directions around said cylindrical tool body.

11. A pipeline inspection tool according to claim 10 wherein said cylindrical body is arranged to move in a linear fashion in a direction of product flow within a pipeline.

12. A pipeline inspection tool according to claim 10 wherein each pole magnet is spiraled in a range of 30° to 150°.

13. A pipeline inspection tool comprising
a first end,
a second end opposite the first end,
and a single primary sensor section positioned between the first and second ends,
the primary sensor section comprising
a substantially rigid frame;
at least one magnet pair, each magnet in the pair spiraling about the substantially rigid frame less than half aturn and being a continuous magnetic pole of opposite polarity from the other magnet in the magnet pair;
at least one sensor,
the at least one magnet pair producing a first magnetic field having an orientation, the orientation being directed obliquely with respect to each of the circumferential and axial directions
wherein the pipeline inspection tool when in use in a pipeline generates one or more oblique magnetic fields each having the orientation, the one or more oblique magnetic fields comprising the first magnetic field and all other magnetic fields that emanate from the pipeline inspection tool and are oriented obliquely with respect to each of the circumferential and axial directions.

14. A pipeline inspection method comprising:
identifying a pipeline defining a circumferential direction and an axial direction and containing an in-line inspection tool comprising
a first end,
a second end opposite the first end,
and a primary magnetic flux leakage sensor section positioned between the first and second ends,
the primary magnetic flux leakage sensor section comprising
at least one magnet pair spiraled about the tool body less than half a turn; and
at least one sensor arranged between the at least one magnet pair,
the at least one magnet pair producing a first magnetic field having an orientation, the orientation being directed obliquely with respect to each of the circumferential and axial directions;
producing relative motion between the at least one magnet pair and the pipeline, the relative motion comprising substantially exclusively translation in the axial direction of the at least one magnet pair with respect to the pipeline;
generating, by the in-line inspection tool during the producing, one or more oblique magnetic fields each having the orientation, the one or more oblique magnetic fields comprising the first magnetic field and all other magnetic fields that emanate from the in-line inspection tool and are oriented obliquely with respect to each of the circumferential and axial directions, the spacing of the at least one magnet pair and the translation in the axial direction during the producing effective for the at least one sensor to detect nominally axially oriented features of the pipeline without requiring induced rotation of the in-line inspection tool; and
collecting, by the at least one sensor during the generating, data characterizing one or more physical characteristics of the pipeline.

15. A pipeline inspection method comprising:
identifying a pipeline defining a circumferential direction and an axial direction and containing an in-line inspection tool comprising:
a first end,
a second end opposite the first end, and
a primary sensor section, the primary sensor section comprising a magnet dipole and at least one sensor, the magnet dipole formed by spaced-apart opposite pole magnets and producing a first magnetic field having an orientation, the orientation being directed obliquely with respect to each of the circumferential and axial directions;
producing relative motion between the magnet dipole and the pipeline, the relative motion comprising substantially exclusively translation in the axial direction of the magnet dipole with respect to the pipeline;
generating, by in-line inspection tool during the producing, one or more oblique magnetic fields each having the orientation, the one or more oblique magnetic fields comprising the first magnetic field and all other magnetic fields that emanate from the in-line inspection tool and are oriented obliquely with respect to each of the circumferential and axial directions, the spacing of the magnet dipole and the translation in the axial direction during the producing effective for the at least one sensor to detect nominally axially oriented features of the pipeline without requiring induced rotation of the in-line inspection tool; and
collecting, by the at least one sensor during the generating, data characterizing one or more physical characteristics of the pipeline.

16. A pipeline inspection method comprising:
identifying a pipeline defining a circumferential direction and an axial direction and containing an in-line inspection tool comprising
a first end,
a second end opposite the first end, and
a primary sensor section, the primary sensor section comprising
a substantially rigid frame,
at least two continuous magnetic poles each spiraling less than half a turn about the substantially rigid frame and
at least one sensor, the at least two continuous magnetic poles producing a first magnetic field having an orientation, the orientation being directed obliquely with respect to each of the circumferential and axial;

producing relative motion between the at least two continuous magnetic poles and the pipeline, the relative motion comprising substantially exclusively translation in the axial direction of the at least two continuous magnetic poles with respect to the pipeline;

generating, by the in-line inspection tool during the producing, one or more oblique magnetic fields each having the orientation, the one or more oblique magnetic fields comprising the first magnetic field and all other magnetic fields that emanate from the in-line inspection tool and are oriented obliquely with respect to each of the circumferential and axial directions, the translation in the axial direction during the producing being effective for the at least one sensor to detect nominally axially oriented features of the pipeline without requiring induced rotation of the in-line inspection tool; and collecting, by the at least one sensor during the generating, data characterizing one or more physical characteristics of the pipeline.

17. The method of claim 16, wherein the primary sensor section further comprises at least one brush contact extending radially outward from each continuous magnetic pole of the at least two continuous magnetic poles.

\* \* \* \* \*

UNITED STATES PATENT AND TRADEMARK OFFICE
CERTIFICATE OF CORRECTION

PATENT NO. : 8,653,811 B2
APPLICATION NO. : 12/572752
DATED : February 18, 2014
INVENTOR(S) : James Simek, Tod Barker and Mark Gregoire Page 1 of 1

It is certified that error appears in the above-identified patent and that said Letters Patent is hereby corrected as shown below:

Title Page: Item (75) please change "Tod Baker" to "Tod Barker"

Signed and Sealed this
Twenty-seventh Day of May, 2014

Michelle K. Lee
*Deputy Director of the United States Patent and Trademark Office*